(12) United States Patent
Kruger et al.

(10) Patent No.: US 7,353,709 B2
(45) Date of Patent: Apr. 8, 2008

(54) METHOD AND SYSTEM FOR DETERMINING MATERIAL PROPERTIES USING ULTRASONIC ATTENUATION

(75) Inventors: Silvio E. Kruger, Brossard (CA); Guy Lamouche, Montréal (CA); Daniel Lévesque, Lachenale (CA); Jean-Pierre Monchalin, Montréal (CA)

(73) Assignee: National Research Council of Canada, Ottawa, Ont. (CA)

( * ) Notice: Subject to any disclaimer, the term of this patent is extended or adjusted under 35 U.S.C. 154(b) by 398 days.

(21) Appl. No.: 11/174,496

(22) Filed: Jul. 6, 2005

(65) Prior Publication Data

US 2007/0006651 A1     Jan. 11, 2007

(51) Int. Cl.
    *G01N 29/11* (2006.01)
(52) U.S. Cl. ...................................................... 73/599
(58) Field of Classification Search .................. 73/599, 73/600
    See application file for complete search history.

(56) References Cited

U.S. PATENT DOCUMENTS

| | | | | |
|---|---|---|---|---|
| 4,026,157 A | * | 5/1977 | Goebbels | 73/865.5 |
| 4,539,848 A | * | 9/1985 | Takafuji et al. | 73/599 |
| 4,597,292 A | | 7/1986 | Fujii et al. | |
| 4,646,748 A | * | 3/1987 | Fujii et al. | 600/441 |
| 4,941,474 A | * | 7/1990 | Pratt, Jr. | 600/437 |
| 5,121,629 A | | 6/1992 | Alba | |
| 5,394,732 A | | 3/1995 | Johnson et al. | |
| 6,109,098 A | * | 8/2000 | Dukhin et al. | 73/64.42 |
| 6,119,510 A | * | 9/2000 | Carasso et al. | 73/61.75 |
| 6,370,956 B1 | * | 4/2002 | Bewlay et al. | 73/599 |
| 6,532,821 B2 | * | 3/2003 | Lamouche et al. | 73/643 |
| 6,672,163 B2 | | 1/2004 | Han et al. | |
| 6,684,701 B2 | | 2/2004 | Dubois et al. | |

(Continued)

FOREIGN PATENT DOCUMENTS

EP     0064399     10/1982

(Continued)

OTHER PUBLICATIONS

"Characterization of Cast Irons By Leaky Rayleigh Surface Acoustic Waves", Proc. Of the 2nd International conference on Emerging Technologies in NDT, Athens, Greece, May 24-26, 1999, eds Van Hemelrijck, Anastassopoulos & Philippidis, Rotterdam (2000).

(Continued)

*Primary Examiner*—Hezron Williams
*Assistant Examiner*—Rose M Miller
(74) *Attorney, Agent, or Firm*—Hans Koenig; J. Wayne Anderson (57) ABSTRACT

A method and system is disclosed for determining a property of an object by measuring ultrasonic attenuation. With the proposed method, a measured ultrasonic interaction signal of the object is compared with a reference signal produced using the same generation and detection setup, but using a reference part. The reference ultrasonic signal has low attenuation, and exhibits equivalent diffraction properties as the object, with respect to a broadband ultrasonic pulse. The difference is attributable to the attenuation of the object. The attenuation as a function of frequency, the attenuation spectrum, is fitted to a model to obtain a parameter useful for identifying one of the many properties of an object that varies with ultrasonic attenuation.

25 Claims, 7 Drawing Sheets

U.S. PATENT DOCUMENTS

| | | | | |
|---|---|---|---|---|
| 7,086,285 B2* | 8/2006 | Reed | ............................ | 73/629 |
| 2004/0060356 A1* | 4/2004 | Scott | ............................ | 73/599 |

FOREIGN PATENT DOCUMENTS

| | | |
|---|---|---|
| JP | 06-188194 | 4/1994 |

OTHER PUBLICATIONS

P. He and J. Zheng, "Acoustic Dispersion and Attenuation Measurement using Both Transmitted and Reflected Pulses", Ultrasonics 39, pp. 27-32, 2001.

E. P. Papadakis, K.A. Flowler and L.C. Lynnworth, "Ultrasonic Attenuation By Spectrum Analysis of Pulses in Buffer Roads: Method And Diffraction Corrections", J. Acoust. Soc. Am. 53, pp. 1336-1343, 1973.

P. Wu and T. Stepinski, "Quantitative Estimation of Ultrasonic Attenuation in a Solid in the Immersion Case With Correction of Diffraction Effects", Ultrasonics 38, pp. 481-485, 2000.

H. Ogi, M. Hirjoa, T. Honda, "Ultrasonic Diffraction From a Transducer With Arbitrary Geometry and Strength Distribution", J. Acoust. Soc. Am. 98, pp. 1191-1198, 1995.

J.-P. Monchalin and J.-D. Aussel, "Ultrasonic Velocity and Attenuation Determination By Laser-Ultrasonics", J. Nondestr. Eval. 9, pp. 211-221, 1990.

B.F. Pouet and N.J.P. Rasolofosaon, "Measurement of Broadband Intrinsic Ultrasonic Attenuation and Dispersion in Solids With Laser Techniques", J. Acoust. Soc. Am. 93, pp. 1286-1292, 1993.

H. Jeong and D.K. Hsu, "Experimental Analysis of Porosity-Induced Ultrasonic Attenuation and Velocity Change in Carbon Composites", Ultrasonics 33, pp. 195-203, 1995.

D.K. Hsu and S.M. Nair, "Evaluation of Porosity in Graphite-Epoxy Composite by Frequency Dependence of Ultrasonic Attenuation", *Review of Progress in Quantitative Nondestructive Evaluation* vol. 6B, ed. By D.O. Thompson and D.E. Chimenti, Plenum Press, New York, pp. 1185-1192, 1987.

M. S. Hugues, S.M. Handley, J.G. Miller and E.I. Madaras, "A Relationship Between Frequency Dependent Ultrasonic Attenuation and Porosity in Composite Laminates", *Reviw of Progress in Quantitative Nondestructive Evaluation* vol. 7B, ed. By D.O. Thompson and D.E.Chimenti, Plenum Press, New York, pp. 1037-1044, 1988.

\* cited by examiner

METHOD AND SYSTEM FOR DETERMINING MATERIAL PROPERTIES USING ULTRASONIC ATTENUATION

BACKGROUND OF THE INVENTION

1. Field of the invention

The present invention relates in general to non-destructive ultrasonic testing, and in particular to a method and system for determining material properties of an object using ultrasonic attenuation.

2. Description of prior art

Ultrasonic attenuation is a measure of the decay of ultrasonic strength during propagation through a material, and can be used to assess properties of materials. For example, the ultrasonic attenuation is directly related to grain size in a polycrystalline solid, e.g. in most metals. The grain size has a strong impact on important mechanical properties of polycrystalline solids. Ultrasonic attenuation can also be used to determine the concentration and size of particles included in a medium, in either a solid or liquid state, or for determining a porosity distribution in a composite material. Another example is the combined use of ultrasonic attenuation and velocity to characterize relaxation behavior and viscoelastic properties of polymeric materials. The physical mechanisms that produce ultrasonic attenuation include scattering and absorption, both of which can be used to characterize material properties. These physical mechanisms (scattering and absorption) are frequency dependent, which is to say that at different frequencies, different attenuation rates are observed. It is known to perform ultrasonic attenuation measurements using a narrowband system (in which case measurement is typically reported at a center frequency), or using a broadband system involving a frequency domain analysis.

One common technique used for attenuation measurement is known as pulse-echo configuration (reflection mode), with ultrasound generated and detected by a piezoelectric transducer coupled to the test object by a couplant or a solid or liquid buffer (i.e. a coupling medium). Another technique is the through-transmission configuration (or transmission mode), where two transducers that face each other on opposite sides of the test object are used for sending and receiving the ultrasound. The through-transmission configuration requires access to both sides of the material. Also according to the through-transmission configuration, the transducer pair must be perfectly matched or fully characterized and preferably aligned with the test object using a coupling medium on both sides. A third technique (known as pitch-catch configuration) involves a pair of transducers separated from each other by a distance, usually on the same side of the test object. The pitch-catch configuration has been used for measuring ultrasonic attenuation of Rayleigh surface waves, Lamb waves, as well as ultrasonic attenuation of bulk waves.

These configurations for attenuation measurement can also be used with non-contact ultrasonic generation and detection techniques, using electromagnetic acoustic transducers (EMATs), air coupled transducers, or laser-ultrasonics. Laser-ultrasonics use one laser with a short pulse for generation of ultrasonic waves. The transfer of energy from the laser to the ultrasonic waves can occur in the thermoelastic regime, where thermal expansion on a surface due to the sudden laser heating is responsible for generating an ultrasonic pulse, or in an ablation regime wherein the laser energy removes a thin layer of the surface, and produces a plasma which induces the ultrasonic waves.

A second laser with longer pulse (or even a continuous wave) is typically used for detection. The second laser illuminates a detection location on the surface of the test object and a phase or frequency shift in the reflected light due to the arrival of an attenuated ultrasonic pulse at the detection location is measured using an optical interferometric system. Interferometric systems for ultrasonic detection known in the art include those based on time-delay interferometry, and systems based on nonlinear optics for wavefront adaptation, as explained by Monchalin J.-P., in "Laser-ultrasonics: from the laboratory to industry", *Review of Progress in Quantitative Nondestructive evaluation* Vol. 23A, ed. by D. O. Thompson and D. E. Chimenti, AIP Conf. Proc., New York, 2004, pp. 3-31. Generation and detection of ultrasound are performed at a distance and eliminate the need for coupling liquid and the alignment requirements of conventional ultrasonics.

Using any of the above configurations, conventional methods of measuring ultrasonic attenuation involve determining a decay of a detected ultrasonic pulse (amplitude) for two propagation distances in the material, e.g. using two echo signals that reverberate between faces of the test object. The attenuation is calculated by comparing amplitudes of the two echoes at each frequency, as explained by A. Vary in Nondestructive Testing Handbook, V. 7, $2^{nd}$ Edition, pp. 383-431 ASNT (1991).

Unfortunately the calculated attenuation is affected by noise of both echoes i.e. uncertainties of both measurements reduce the accuracy of the attenuation value. When the test object is thick and/or made of high attenuation material, the second echo has a poor signal-to-noise ratio (SNR). In such cases, the two-echo attenuation method may not permit accurate measurement, and the SNR of the first echo is not fully exploited. Given the limitations of the conventional two-echo method, the use of a single echo approach to determine ultrasonic attenuation is strongly desirable. However, the amplitude of an echo is also dependent on the generation strength, coupling efficiency, detection efficiency, etc. In the conventional two-echo method, the comparison with an echo inherently accounts for all of these factors, providing a normalized reading.

Another difficulty with the conventional two-echo method is the need for correction of diffraction effects of the ultrasonic pulse to obtain the intrinsic ultrasonic attenuation that is attributable to the test object. While simplified theoretical models have been used to calculate a correction for diffraction for simple geometries of the test object, the diffraction behavior in real situations can be more complex.

The elimination of variations caused by the generation strength, coupling efficiency, detection efficiency, and diffraction to produce a fully normalized intrinsic ultrasonic attenuation spectrum is the most challenging task for the use of a single echo to determine material properties. For some embodiments of the pulse-echo configuration, normalization may be performed using the ultrasonic pulse that is reflected by the surface of the test object (i.e. an entrance echo) to characterize the strength of the generated ultrasonic pulse, permitting the amplitude of the single echo interaction signal to be used. For the through-transmission configuration, normalization is often made by comparison with the pulse propagating through the coupling medium in the absence of the test object. This configuration requires access to both sides of the material, which may not be possible, or preferred, in some industrial applications. Furthermore, the use of an entrance echo, or sample removed reading in the above cases does not remove the need for diffraction correction to obtain the intrinsic material attenuation. A model is still required with the precise knowledge of the characteristics of the system used.

The use of a single echo in a laser-ultrasonic technique to measure a material property in comparison with attenuation of a reference material is taught in the U.S. Pat. No. 6,684,701 to Dubois et al. Dubois et al. teach a method for ultrasonic measuring of porosity of a sample composite material by accessing only one side of the sample composite material. The method involves measuring a sample ultrasonic signal from the sample composite material, normalizing the sample ultrasonic signal relative to the surface displacement at generation on the sample composite material, and isolating a sample back-wall echo from the sample ultrasonic signal. A sample frequency spectrum of the sample back-wall echo is then determined. Next, the method includes the steps of measuring a reference ultrasonic signal from a reference composite material, normalizing the reference ultrasonic signal relative to the surface displacement at generation on the reference composite material, and isolating a reference back-wall echo from the sample ultrasonic signal. A reference frequency spectrum of the reference back-wall echo is then determined. The invention further includes deriving the ultrasonic attenuation of the sample composite material as the ratio of the sample frequency spectrum to the reference frequency spectrum over a predetermined frequency range. Comparing the derived ultrasonic attenuation to predetermined attenuation standards permits the evaluation the porosity of the sampled composite material.

The method of Dubois et al. is limited to the pulse-echo configuration described above. According to Dubois et al., it is necessary to compensate for variance in the generation strength and detection efficiency, by comparing the amplitude with a surface displacement at generation on the surface of the test object to normalize each echo. This approach can only be applied to laser-generated ultrasound in the thermoelastic regime. Further the method according to Dubois et al. does not account for variations caused by penetration of light through the surface of the test object. Unfortunately the surface displacement is not an accurate measure of energy of the ultrasonic pulse, as it does not account for contributions from penetrating light. For example, in carbon-epoxy composites, the light penetration of the ultrasonic generating laser is dependent upon the thickness of a superficial epoxy layer, which in practice, varies considerably and is difficult to determine. Also, normalization using surface displacement is not applicable for laser-generated ultrasound in the ablation regime where the generation laser produces a plasma. While a strong signal may be detected at generation (particularly when the pulse echo method is used), the strong signal, while including a contribution of the surface displacement, is primarily caused by a refractive index perturbation of plasma, which is highly variable, and cannot be relied upon to gage the strength of the ultrasonic pulse.

There therefore remains a need for a method and system for deriving an ultrasonic attenuation measurement using a single echo that compensates for diffraction.

SUMMARY OF THE INVENTION

According to the present invention there is provided a method and a system for using ultrasonic attenuation to determine a material property of an object from a single detected ultrasonic pulse propagated through the material. The invention can be applied to any ultrasonic technique (e.g. piezoelectric transducers, laser-ultrasonics and EMATs), for any type of wave (e.g. longitudinal, shear and surface waves) and any generation/detection configuration (e.g. pulse echo, through-transmission, and pitch-catch). For a given technique, wave mode and configuration, measurements are performed on the material being investigated and also on a reference material. The reference material is used to characterize the response of the whole system of measurement (bandwidth, diffraction, etc.), except for the intrinsic attenuation of the test material and the possible changes in signal strength.

Accordingly a method for using ultrasonic attenuation to determine a material property of an object is provided. The method involves receiving an interaction signal from an ultrasound detector. The interaction signal captures at least one manifestation of a broadband ultrasonic pulse impinging on a detection location of the object after the ultrasonic pulse has propagated in the object. In propagation through the object, the ultrasonic pulse is attenuated by one or more physical mechanisms.

A portion of the interaction signal corresponding to the attenuated ultrasonic pulse is transformed from the time domain to the frequency domain, to obtain an amplitude spectrum. The portion may be determined by identifying a part of the interaction signal that corresponds to a single manifestation of the broadband ultrasonic pulse impinging on the detection location. When there are multiple echos in the interaction signal, a strongest one may be selected. Determining the portion of the interaction signal may involve applying a window selection function for selecting part of the interaction signal that corresponds to a single manifestation of the broadband ultrasonic pulse impinging on the detection location. For example, cross-correlation of a standard profile of an ultrasonic pulse with the interaction signal may be used to center the manifestation within the window. Prior knowledge of the test object may be used to determine a coarse time window of the interaction signal to narrow a search of the portion within the interaction signal.

Once the amplitude spectrum is obtained, it is compared with a reference amplitude spectrum to obtain an attenuation spectrum. The reference amplitude spectrum produced in a similar manner as the amplitude spectrum using a reference piece. The reference piece has equivalent diffraction properties as the object with respect to the broadband ultrasonic pulse, but the reference amplitude spectrum is substantially free of attenuation, either because the reference piece has known attenuation parameters which are used to correct for attenuation in the amplitude spectrum of the reference piece, or because the reference piece is selected to provide negligible attenuation. For example, the reference piece may be selected to have a shape that matches the test object, and to be made of a material having an ultrasonic velocity matching that of the test object, but having substantially no attenuation.

The attenuation spectrum is fit to a model of frequency dependent attenuation to obtain an attenuation parameter. The attenuation parameter can then be used to compute a material property of the object that depends on the attenuation. The determination of a best fit of the attenuation spectrum may involve using a model that accounts for frequency independent variations of signal strength between the test material and the reference material. In particular, the model may account for frequency independent variations of signal strength by using a derivative of the attenuation spectrum to obtain an attenuation parameter.

For example, determining the best fit may involve comparing the measured attenuation spectrum to curves of the form: $\alpha(f) = \alpha_0 + af^m + bf^n$ where $\alpha_0$ is an arbitrary amplitude offset that accounts for variations in signal strength, m and n are frequency powers associated with respective underlying mechanisms of the attenuation, and the parameters a and b are representative of contributions from the mechanisms involved relating to material properties. The parameter a is zero if there is only a single underlying mechanism for the attenuation. Fitting may involve varying the attenuation parameters while keeping m and n fixed.

The steps of receiving and transforming may be repeatedly applied to a plurality of interaction signals from the object, and the method may further comprise computing a mean of the plurality of signals, which serves as the attenuation spectrum.

The method may further involve validating the interaction signal and amplitude spectrum using rejection criteria in both time and frequency domains.

The method may further involve using a calibration curve to relate the attenuation parameter to a property of the object. The material property may be, for example, grain size in a polycrystalline solid, or porosity of a composite material.

A system for measuring ultrasonic attenuation to determine a material property of an object is also provided. The system involves an ultrasonic pulse generation and detection set up for launching a broadband ultrasonic pulse into the object, and detecting the pulse after propagation through the object, a receiver for digitizing an interaction signal of the detected ultrasonic pulse; and a signal processor. The signal processor is adapted to transform a part of the interaction signal corresponding to a single manifestation of the detected pulse from the time domain into the frequency domain to obtain an amplitude spectrum.

The signal processor computes an attenuation spectrum by comparing the amplitude spectrum with a reference amplitude spectrum. The reference amplitude spectrum being derived from a reference piece having equivalent diffraction properties as that of the object. The reference amplitude spectrum has substantially no attenuation. The signal processor fits the attenuation spectrum to a model to determine an attenuation parameter used for determining a property of the object.

The signal processor may further be adapted to compute a mean of a plurality of interaction signals from the object at one or various locations to produce the amplitude spectrum. The signal processor may further be adapted to perform a time or frequency domain averaging process of the plurality of interaction signals to produce the amplitude spectrum.

The system may further include a controlled motion system for scanning over a surface of the object. The signal processor may further use attenuation parameters to create an image of the material property of the object.

The ultrasonic pulse generation and detection set up may include a generation laser for generating the broadband ultrasonic pulse, and a detection laser coupled to an optical detection system for detecting the manifestation of the broadband ultrasonic pulse. The generation laser and detection laser may be directed onto a same side of the test object.

BRIEF DESCRIPTION OF THE DRAWINGS

A better appreciation of the present invention and advantages thereof is provided having regard to the following description in conjunction with reference to the accompanying drawings in which like reference numerals identify like features. In the accompanying drawings:

FIG. 2b is a block diagram of a method for obtaining a reference spectrum used in the method of FIG. 2a;

DETAILED DESCRIPTION OF THE PREFERRED EMBODIMENTS

The present invention provides a method and system for measuring ultrasonic attenuation in a test object using a detected, attenuated broadband ultrasonic pulse. The method permits a measurement to be based on the attenuated broadband ultrasonic pulse without considering further echoes, surface displacement, etc. In effect the single detected, attenuated broadband ultrasonic pulse is effectively normalized by comparison with a reference broadband ultrasonic pulse that compensates for diffraction and geometric parameters of the test object. The reference broadband ultrasonic pulse is obtained in a reference sample having equivalent diffraction properties as the test object, with respect to the broadband ultrasonic pulse. The comparison with the reference may be made in the frequency domain by dividing a detected spectrum with a reference spectrum. Importantly the reference spectrum has substantially no attenuation, either because the attenuation through the reference sample is negligible, or because the attenuation in the reference sample is fully characterized and therefore removed from the reference spectrum.

The proposed method is particularly efficient with a broadband ultrasonic system having good response at low frequencies. Also, the method requires that the attenuation to be measured varies with frequency, which is the case for most mechanisms of ultrasonic interaction with materials.

Figure 1:
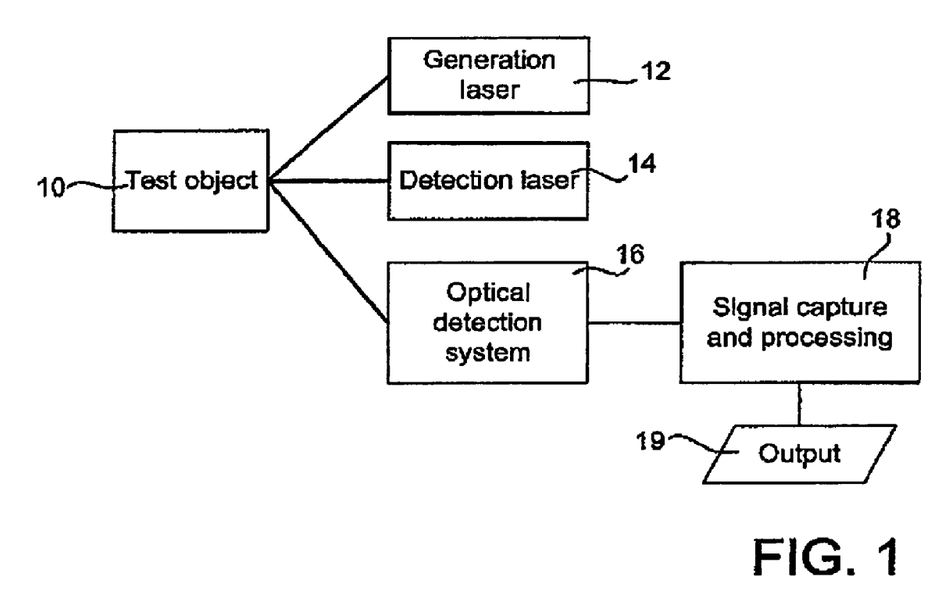
FIG. 1 is a schematic diagram of a system according to one embodiment of the invention.

FIG. 1 shows an apparatus according to one embodiment when applying the proposed ultrasonic attenuation method. In broad terms, the apparatus includes a system for generating a broadband ultrasonic pulse in a test object 10, a system for detecting the broadband ultrasonic pulse after transmission through a part of the test object 10, and signal processor that are coupled to measure the attenuation of the test object 10. The test object 10 under study can be of any geometrical shape, and depending on the configuration used, only one side of the test object 10 needs to be accessible.

The illustrated system includes a generation laser 12 for generating a broadband ultrasonic pulse, although it will be appreciated that in alternative embodiments, other generation means can be used, including those identified above. In currently preferred embodiments, the generation laser 12 is a pulsed laser that operates in either the ablation or thermoelastic regime for inducing an ultrasonic pulse in the test object 10. Suitable wavelength and power densities of the pulsed laser, and generation location on the surface of the test object 10 can be selected according to the material and configuration to produce an ultrasonic pulse in the test object 10 having desired properties.

The system for detecting the broadband ultrasonic pulse may include a detection laser 14, and an optical detection system 16. The detection laser 14 may be a long pulse laser, or a continuous laser that directs a beam onto a detection location on the surface of the test object 10. As noted above the detection location and generation location are the same in the pulse-echo configuration, are opposed surfaces in the through transmission configuration, and are separated by a distance (usually on the same surface) according to the pitch-catch configuration. The detection laser 14 may be a relatively high powered laser to compensate for a relatively poor reflectivity of the test object 10 at the detection location, and still provide adequate optical power for detection.

In some embodiments, it is preferable that the generation laser 12 and/or the detection laser 14 and optical detection system 16 are movable with respect to the test object 10 to perform ultrasound measurements at a plurality of pairs of generation and detection locations. Multiple measurements could be used separately for detecting physical properties of the test object 10 at different locations, and/or can be combined for spatial averaging to produce a mean measure of the physical property of the test object with higher accuracy. This can be done by moving the test object 10, by moving the apparatus, or by moving optical devices, for example.

The detection laser 14 is coupled to the optical detection system 16, which may be a time-delay interferometer, such as a stabilized confocal Fabry-Perot interferometer, or may include non-linear optical components for wave front adaptation, as introduced above. The optical detection system 16 outputs an electrical interaction signal to a signal capture and processor unit 18. For example, the signal capture and processor unit 18 may include an analog to digital signal converter (A/D) for digitizing the electrical interaction signal.

The signal capture and processor 18 is adapted to transform the interaction signal from the time domain to the frequency domain, for example by application of the Discrete Fourier Transform to the interaction signal to produce an amplitude spectrum of the detected ultrasonic pulse. Preferably a Fast Fourier Transform algorithm well known in the art is used. In preferred embodiments, only a part of the interaction signal is transformed, the part being selected by a window selection function that ensures that only the relevant ultrasonic echo is represented in the amplitude spectrum, and that multiple reflections or echoes are not compounded.

The signal capture and processor 18 is further adapted to produce an attenuation spectrum by comparing the amplitude spectrum of the test object 10 with that of a reference object. The reference amplitude spectrum is produced in the same manner as that of the test object 10. In some embodiments, the reference object is of a same geometry as the test object 10, and has similar diffraction properties, but the broadband ultrasonic pulse exhibits substantially no attenuation in propagation through the reference object. Alternatively an equivalent reference amplitude spectrum can be obtained using a reference object having different geometry but with equivalent diffraction properties. The low-attenuation reference amplitude spectrum can also be produced with a reference object having a well characterized attenuation by correcting the detected amplitude spectrum using equations known in the science of ultrasonics.

The signal capture and processor 18 also fits the attenuation spectrum to a model. A best fit of the attenuation spectrum of the test object to a curve of the model provides at least one attenuation parameter of the test object. One or more attenuation parameter is then used to derive a physical property of the test object that varies with ultrasonic attenuation. Preferably the signal capture and processor 18 has access to a memory for storing the interaction signals, amplitude spectra, attenuation spectrum, attenuation parameters, and the derived physical property as well as program instructions for carrying out the processing thereof. At least the derived physical property is subsequently output 19. One or more of the stored information may be displayed graphically or numerically by a display unit or other output device, for example. The signal capture and processor 18 may include a general purpose computer.

Figure 2A:
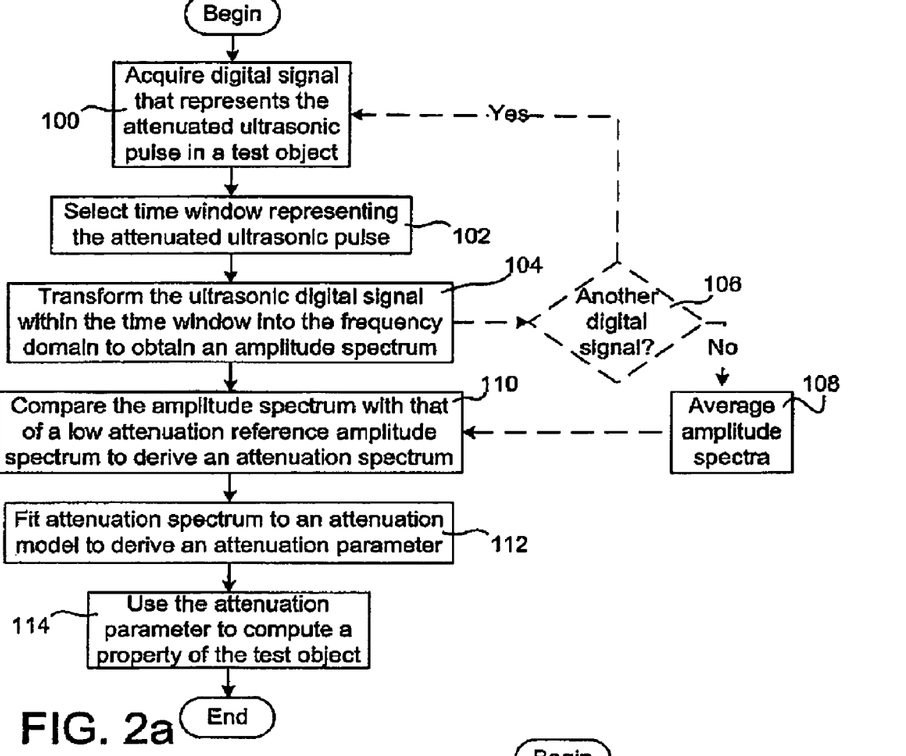
FIG. 2a is a block diagram of a method for determining a material property using ultrasonic attenuation.

FIG. 2a shows an embodiment of a method for measuring ultrasonic attenuation. For clarity of explanation, FIGS. 3a,b, 4a,b and 5a,b are referred to in description of associated steps. In step 100, an interaction signal representing an attenuated broadband ultrasonic pulse is received, for example from an optical detection system 16 shown in FIG. 1 via signal reception hardware. The interaction signal is time varying amplitude signal, where the amplitude is related to the surface movement due to the arrival of the ultrasonic waves at the detection location on the surface of the test object.

Figure 3A:
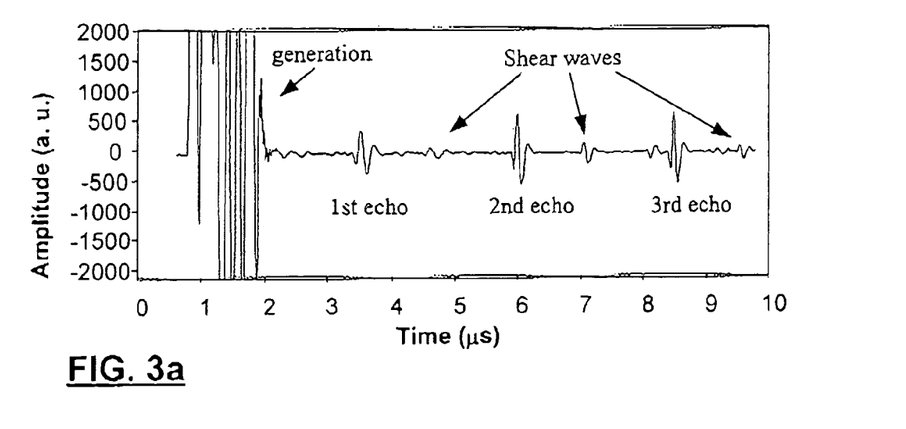
FIG. 3a is an example of a time domain ultrasonic interaction signal obtained using a laser-ultrasonic system.

An example of an interaction signal detected using the apparatus of FIG. 1 in the pitch-catch configuration is illustrated in FIG. 3a. The interaction signal begins with a generation perturbation in which the optical detection system 16 is bombarded with spurious reflected light from the generation laser, or the detection light is strongly modulated by the plasma produced. The generation artifacts can be exacerbated by the use of a common wavelength for both the generation and detection lasers. Subsequently, the interaction signal shows first, second, and third echoes of a broadband ultrasonic pulse. In the illustrated interaction signal of FIG. 3a, a pitch-catch configuration was used in a low attenuation material. Strong diffraction effects in this configuration result in a first echo that is of lower amplitude than the second and third echoes. Because of the strong initial diffraction in such embodiments, a second echo of the ultrasonic pulse having a higher quality may be used for attenuation measurements. It is also noted that shear waves are manifest on the interaction signal. It is assumed for illustration that longitudinal waves are used for the measurement, however it will be appreciated that other ultrasonic waves could alternatively be used in other embodiments. It will be noted that the method can be applied to any mode of ultrasonic waves (longitudinal, shear, surface, etc.) in any configuration (pulse echo, through-transmission, pitch-catch, etc.).

Accordingly there is a need for a mechanism for identifying the desired part of the interaction signal to be analyzed. Applicant currently prefers using a window selection function to identify a portion of the interaction signal that is associated with a single manifestation (echo) of the desired ultrasonic pulse (step 102). Herein the portion of the interaction signal that constitutes a single manifestation of the ultrasonic pulse is referred to as an echo, even if, in accordance with the through-transmission configuration, the ultrasonic pulse is not bounced off of any wall. It is preferable, if the thickness and ultrasonic velocity of the material are roughly known, to narrow the search by pre-selecting a coarse time window of the echo. Then, to help identification of the echo from adjacent noise and centering in a narrow time window, a cross-correlation method involving comparison with a standard profile of an ultrasonic pulse can be used. The amplitude of a peak of the echo may be compared with a noise level determined in a conventional manner, to determine whether the echo is usable. An interaction signal may be rejected if a quality the echo is too low.

Figure 3B:
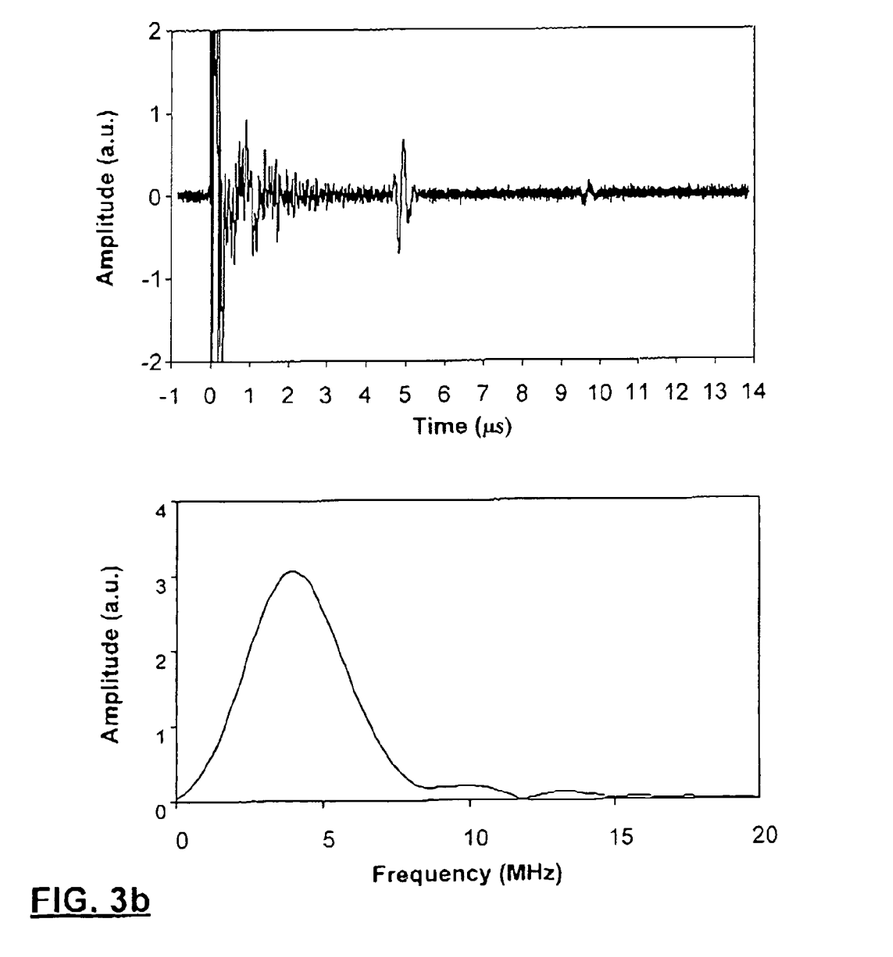
FIG. 3b is an example of window of a laser-ultrasonic interaction signal and corresponding amplitude spectrum.

The echo is then represented in the frequency domain by application (step 104) of the Discrete Fourier Transform (DFT), deriving an amplitude spectrum. For example, the Fast Fourier Transform (FFT) algorithm can be used. Rejection criteria are used both in the time domain, to ensure that the echo is discernable over a noise (as noted above), and in frequency domain, where similarity with an expected spectrum shape (e.g. Gaussian) is used to determine whether to accept or reject an amplitude spectrum. It will be apparent to those of skill in the art that the interaction signal is subjected to signal processing techniques to prevent aliasing and to minimize spectral leakage, as is commonly practiced in the art. FIG. 3*b* schematically illustrates a time-domain interaction signal, where an echo, indicated as Echo A, is selected and centered within a time window, and the amplitude spectrum is obtained. The pulse-echo configuration was used to produce this interaction signal.

In some embodiments, it will be preferable to calculate a mean of multiple amplitude spectra measurements to provide a higher accuracy measurement, for example if the amplitude spectrum of the echo of the ultrasonic pulse has a SNR insufficient to provide an attenuation spectrum of a quality required to reliably determine material property of the test object. While the averaging may be performed in the time domain using the interaction signal, it is currently preferred to perform addition in the frequency domain. By averaging multiple spectra, a higher quality amplitude spectrum may be produced. The accuracy of the window selection function is of greater importance when averaging multiple spectra, because the window selection function ensures that the echoes are substantially synchronized. That is, the window selection function temporally aligns the different echoes so that precisely gated echoes are used to produce the amplitude spectra, minimizing errors due to any superposition offset.

For example, the window selection function has advantages if compensation for thickness variation of the test object at different generation and detection locations is required. It will be appreciated that a difference in thickness of the test object at the detection and generation locations results in different time between generation of the ultrasonic pulse, and manifestation of the pulse at the detection location. If such thickness variation exists, each echo may not be temporally aligned and the sum of digital signals would not produce an aggregate digital signal of decent quality. The window selection function is one mechanism for eliminating errors caused by temporal offset of the spectra.

It will be appreciated that many different types of mean computations can be applied. Applicant currently prefers frequency domain averaging using complex spectra, i.e. including amplitude and phase information from the FFT output. The smoothness of the resulting amplitude spectrum is indicative of the improvement. It will be appreciated that averaging of measurements at various positions presents some advantages in certain situations. For example, if coherent noise is present at a phase offset that varies with the position of the detection location on the surface of the test object, averaging at multiple detection locations will statistically improve the SNR. One example of such coherent noise is coherent backscattered grain noise present in the interaction signal of a polycrystalline material.

Accordingly, optional steps 106-108 may be applied to perform the averaging. In step 106 it is determined whether there is another amplitude spectrum to be averaged. If another amplitude spectrum is to be averaged, the process returns to step 100. The number of amplitude spectra needed to provide an acceptable attenuation spectrum can be established empirically, and is subject to accuracy requirements related to different applications. Once the last amplitude spectrum is obtained, the amplitude spectra are averaged in step 108 and the average amplitude spectrum is processed in step 110.

Figure 4A:
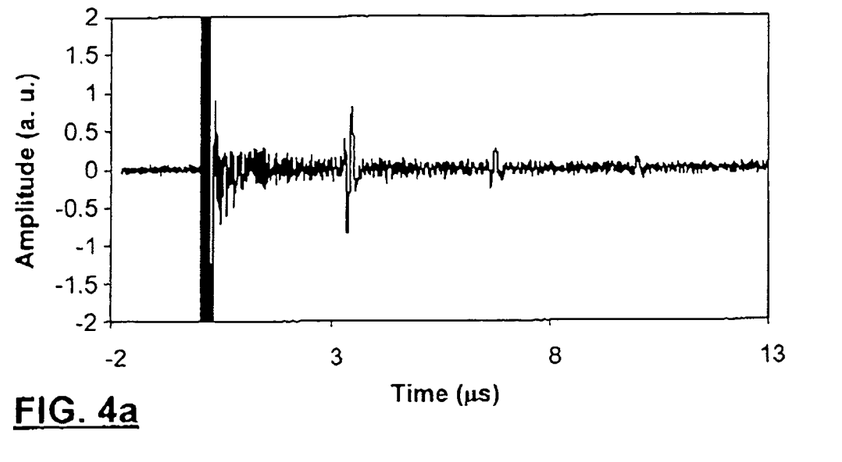
FIG. 4a is an ultrasonic interaction signal obtained from a single measure at a detection location on an object.
Figure 4B:
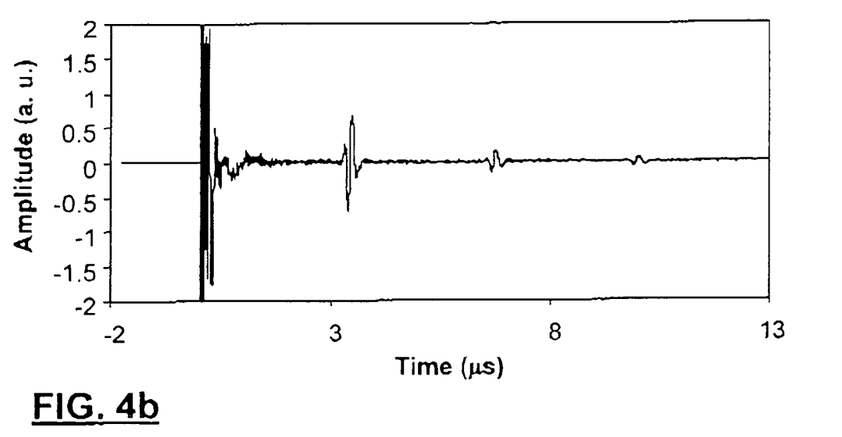
FIG. 4b is an averaged ultrasonic interaction signal taken from measurements at twelve locations on the object.

FIGS. 4*a,b* schematically illustrate the effect of averaging for reducing noise in the interaction signal. In FIG. 4*a* a single interaction signal is shown as received, whereas twelve interaction signals are averaged in the time domain to produce the mean interaction signal shown in FIG. 4*b*. The twelve signals are added in the time domain without windowing, and are temporally aligned with respect to ultrasonic generation, which is adequate, for example, when taking a mean of measurements at same generation and detection locations, or otherwise when the thickness does not vary with each measurement. It will be appreciated by inspection by those of skill in the art that FIG. 4*b* illustrates an improved SNR over that of FIG. 4*a*.

In step 110, the amplitude spectrum of the test object is compared with that of a reference object. As explained above, the reference amplitude spectrum may be produced by application of steps 100-108 to a reference object in lieu of the test object, where the reference object has diffraction properties equivalent (in relation to ultrasonics) to those of the test object, but has substantially no attenuation. Accordingly the reference amplitude spectrum can be derived using the method described below with reference to FIG. 2*b*.

More specifically, the attenuation of ultrasound waves in the test object as a function of frequency, (i.e. the attenuation spectrum), is computed as the ratio between the spectrum of the reference object to that of the test object. Typically the attenuation is a function of distance traveled by the wave, and accordingly the attenuation spectrum may be divided by the distance through which the ultrasonic pulse traveled in the test object. This distance may be predetermined, measured mechanically, or may be computed by the travel time between generation and detection, or the time between echoes, as will be appreciated by those of skill in the art.

For example, to compute the attenuation spectrum in decibel units the following equation can be used:

$$\alpha(f) = \frac{20}{d} \log_{10}\left(\frac{Aref(f)}{A(f)}\right) \quad (1)$$

where f is the frequency, $\alpha$ is the obtained attenuation spectrum, d is the distance traveled by the ultrasonic pulse, Aref(f) is the amplitude spectrum of the signal obtained in the reference material having low (negligible) attenuation, and A(f) is the amplitude spectrum of the test material. It will be noted that the attenuation spectrum α is a relative attenuation measurement with respect to the reference material. An absolute attenuation spectrum is not required to assess material properties, when the attenuation spectrum is fitted to a model as described below. If the reference material presents some known attenuation, such attenuation is simply removed from Aref in Eq. (1).

Figure 5A:
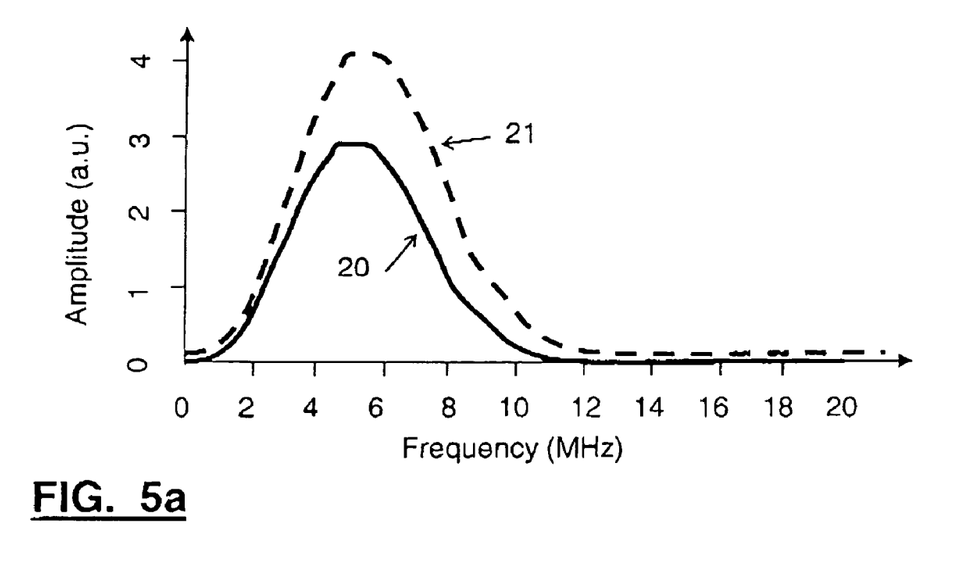
FIG. 5a is an example of object and reference amplitude spectra.

FIG. 5a illustrates a typical example of an amplitude spectrum 20 for a test object, and a reference amplitude spectrum 21. It will be noted that the reference amplitude spectrum 21 is of greater amplitude than the amplitude spectrum 20. While this happens whenever the same conditions are applied for both the test object and the reference object, it will be appreciated that it is not necessary within the context of the invention. If the sensitivity of the ultrasound detector, or the strength of the ultrasound generator is different, the system of the present invention can use a model that compensates for an arbitrary amplitude offset. The attenuation spectrum is then, in step 112 fitted to a model of attenuation. Because the attenuation spectrum is a relative measure rather than an absolute attenuation measurement, the attenuation spectrum does not account for amplitude variations that are independent of frequency. The fit is therefore preferably performed with a model that accounts for possible variations in pulse strength at generation, and detection sensitivity, between the test material and the reference (i.e. an amplitude offset).

Many physical mechanisms that are responsible for attenuation can be modeled by a power law dependence on frequency. If one such mechanism is present, the measured attenuation can be fitted to the following model:

$$\alpha(f)=\alpha_0+bf^n \qquad (2)$$

where n is a frequency power, $\alpha_0$ is a parameter that accounts for variations in signal strength independent of frequency, and b represents a physical attenuation mechanism relating to a material property. It will be appreciated that for any two parameters $\alpha_0$, b of the model defines a curve. A measure of fit of the attenuation spectrum to a curve is compared for different curves. The curve for which the measure of fit is optimal is determined to be the best fit of the attenuation spectrum to the model, in a manner well known in the art. As a result of the fitting, the attenuation parameters $\alpha_0$ and b are determined.

The parameter $\alpha_0$ is not needed for determining a physical property of the test object, and unless contributions to this offset can be identified, $\alpha_0$ does not correspond to any relevant parameter of the system. Accordingly, the attenuation value offset of the attenuation spectrum may be ignored. The model defined above permits identification of the frequency-varying attenuation without requiring correction for variances in signal strength. For robustness, the parameter n is preferably kept fixed during the fitting procedure, with a value ranging between 0 to 4. For example, if the predominant mechanism involved is scattering in the Rayleigh regime, the value of n is 4, corresponding to an attenuation that depends on the fourth power of the frequency.

If two physical mechanisms contribute to attenuation, such as scattering and absorption, the measured attenuation can be fitted to the following function:

$$\alpha(f)=\alpha_0+af^m+bf^n \qquad (3)$$

where m and n are the frequency powers, respectively for absorption and scattering. Similarly, the parameters a and b are factors of the two mechanisms involved relating to material properties. According to well accepted models of absorption and scattering, m is between about 0.2 to about 1.5 and n is between about 1.5 to about 4. Again, for robustness, m and n are preferably kept fixed during fitting, and should not be too close. If both frequency powers n and m are close, Eq. (2) must be used, with n being an effective frequency power for both mechanisms involved, in which case contributions from each mechanism cannot be identified. It will be appreciated that only one or more of the parameters may be needed for computing the physical property of the test object.

Also with the above function, the parameter $\alpha_0$ that accounts for variations in signal strength could be simply estimated by inspection and kept fixed while applying the fitting procedure.

Figure 5B:
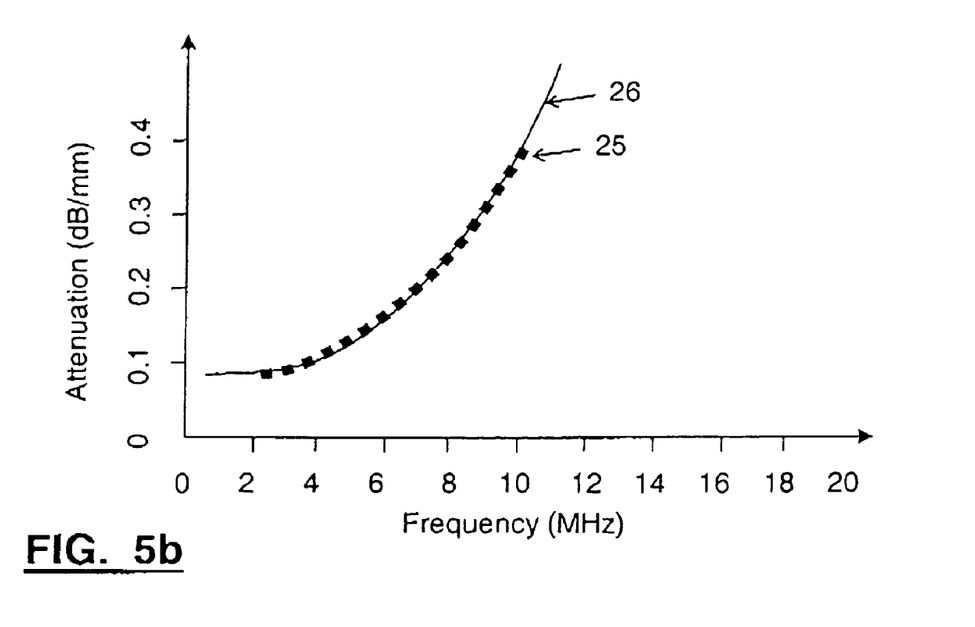
FIG. 5b is an attenuation spectrum measured and fitted with a model.

FIG. 5b illustrates an attenuation spectrum measured 25 and fitted to a model 26. The measured attenuation spectrum 25 is a relative attenuation measurement with respect to the reference attenuation spectrum. It will be appreciated that a curve 26 conforming with the model that best fits the attenuation measurement 25 is one of many curves of the model. The fit with curve 26 provides both the offset measure, and a parameter that allows assessment of at least one material properties of the test object.

In some applications, a material property that varies with a first derivative of the attenuation spectrum is required. This removes the constant factor $\alpha_0$ that relates to variations in signal strength between the test material and the reference. The derivative of attenuation spectrum can be obtained numerically using methods well known in the art.

Figure 2B:
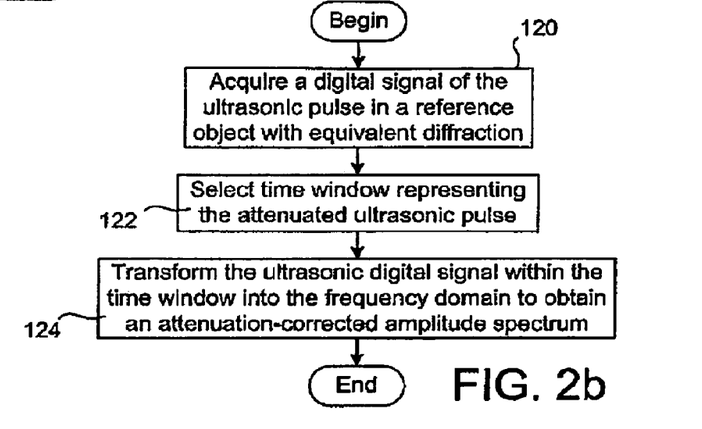

FIG. 2b shows an embodiment of the method for producing a reference amplitude spectrum. In step 120, an interaction signal is acquired that represents the ultrasonic pulse after transmission through a path in a reference object. The reference object has fully characterized attenuation properties (preferably negligible attenuation) and the path in the reference object has equivalent diffraction properties as the path through the test object used in FIG. 2a. The reference amplitude spectrum is used to correct for the response of the whole system (bandwidth, diffraction, etc.). By appropriate selection of the reference material, the diffraction effect can be made nearly identical in both signals and is consequently automatically removed by comparison with (division by) Aref. To have equivalent diffraction behavior, the reference material may be chosen to have the same geometry and ultrasonic velocities, or a combination of those parameters to provide equivalent diffraction conditions, as will be understood by those skilled in the art. The reference amplitude spectrum preferably uses exactly the same generation and detection procedure as applied to the test object.

In step 122, a procedure is applied, as described above, to identify a time window (i.e. a portion of the interaction signal corresponding to a desired echo or like manifestation of the broadband ultrasonic pulse). Subsequently the interaction signal within the time window is transformed into the frequency domain (step 124) to produce the reference amplitude spectrum. If the reference object exhibits negligible ultrasonic attenuation, the reference amplitude spectrum is computed by applying the DFT or FFT to the signal. Otherwise the characterized attenuation is used to correct the produced amplitude spectrum to construct the non-attenuated reference amplitude spectrum, in a manner that is familiar to those skilled in the art and science of ultrasonics. It will be appreciated that an extent of the attenuation correction may be reduced by using lower attenuation reference materials.

In a manner similar to that described above for the test object, the spectrum of the reference object may be averaged by multiple measurements taken at one or more locations.

Exemplary Applications

There are numerous applications of the proposed method and system.

A first example is the determination of grain size of steel on a production line, using laser-ultrasonic attenuation measurement. Very often, austenitic grain size associated with austenite decomposition during cooling is the most important metallurgical parameter for determining the mechanical properties of steels. In order to correctly apply controlled thermo-mechanical processing of a steel piece, the austenitic grain size of the steel piece must first be determined. The ability to determine the austenitic grain size in the production line is therefore highly sought after technology.

The method described above was used to quantitatively determine austenitic grain sizes from ultrasonic attenuation for a wide range of grain sizes (20 to 300 µm) and for relatively thick materials (up to 30 mm) in seamless steel tubes. The system consisted of a Q-Switched Neodymium: Yttrium Aluminum Garnet (Nd:YAG) laser for generation of the ultrasonic pulse and a long pulse Nd:YAG laser for detection in a pitch-catch configuration. The detection light modulated by the ultrasonic pulse incident in the detection location is demodulated by a Fabry-Perot interferometer.

For calibration, steel samples of different grades were heated in a Gleeble thermomechanical simulator in the range of 900° C. to 1250° C. and held for about 10 minutes to saturate grain growth. Throughout the whole thermal cycle, laser ultrasonic measurements were performed. After quenching for an appropriate time (according to the steel grade) the former austenitic grains were revealed by etching and quantitatively characterized by image analysis. Measurement was also performed on a reference sample of steel having a same geometry and ultrasonic velocity, and having low attenuation to obtain the reference amplitude spectrum.

Figure 6:
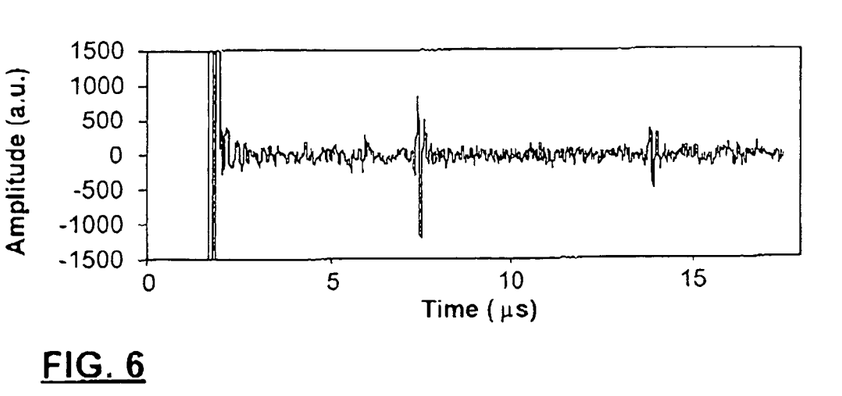
FIG. 6 shows an interaction signal obtained in a grain size measurement application.

FIG. 6 illustrates a interaction signal corresponding to a detected ultrasonic pulse on a production line implementation for grain size determination. The configuration of the generation and detection equipment was the pitch-catch configuration described above.

Figure 7A:
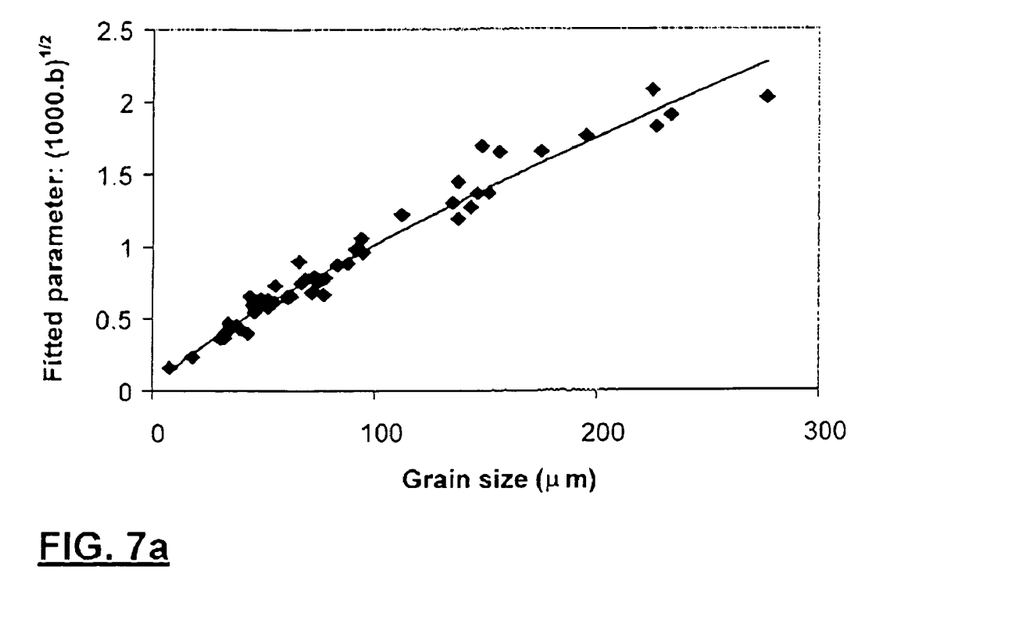
FIG. 7a is an example of a calibration curve for a fitted attenuation parameter 'b'.

FIG. 7a is a graph of an example of a calibration curve for interpreting mean grain size with results of the ultrasonic attenuation parameter b, where b is obtained by fitting the attenuation spectrum to a model. The grain size is obtained using standard metallographic techniques.

There were many barriers to accurate on-line measurements for applications in industrial environments using real products. As the tube surfaces reflected poorly the detection laser light, SNR was a significant problem. To improve the attenuation spectrum quality, amplitude spectra were computed by averaging ultrasonic interaction signals obtained at many positions along the tube, and so the grain size was evaluated over a segment of the tube or over the whole tube. The frequency domain averaging procedure described above using complex spectra was found to be adequate.

Figure 7B:
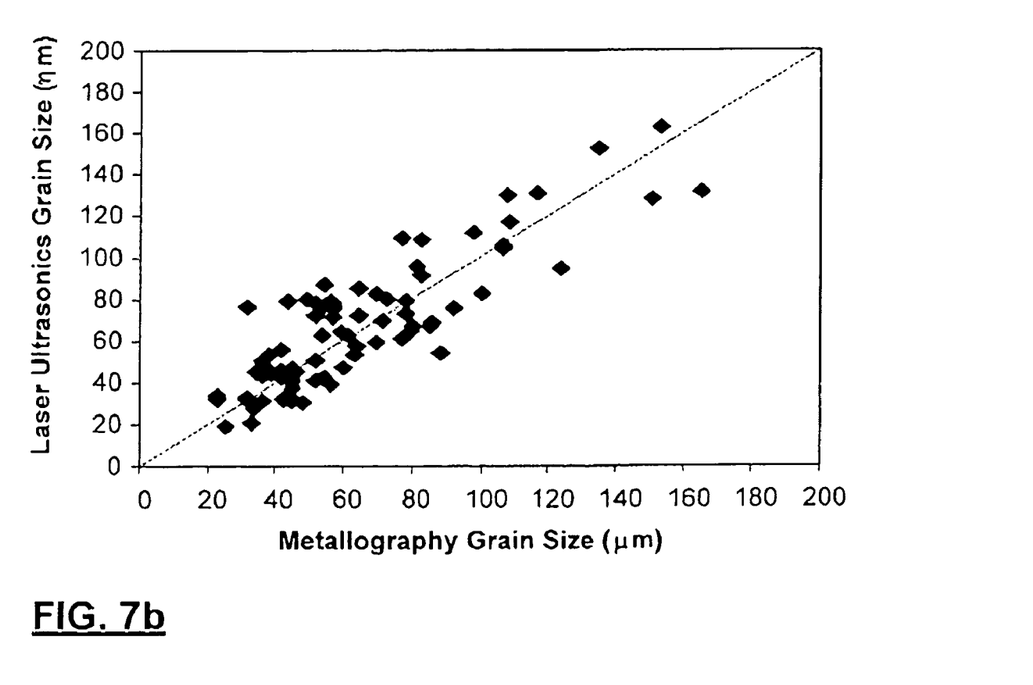
FIG. 7b is a graphical comparison between grain sizes measured on-line by a laser ultrasonic system versus those obtained by metallography.

FIG. 7b shows the comparison between austenitic grain size measured on-line by the laser-ultrasonic system and interpreted using the calibration curve of FIG. 7a, and that obtained by metallography on the same tubes after proper quenching. Due to the production line conditions, the ultrasonic measurements were expected to be less accurate that those performed in controlled laboratory conditions. Accuracy of the grain size measurements using metallography was reduced because of difficulties inherent in applying, in the production environment, the proper cooling procedure that allows the 'decoration' of former austenitic grain sizes. With estimated metallographic grain size accuracy between 0.5 and 1 ASTM, a statistical analysis shows that the laser-ultrasonic grain sizes determined on-line had at least the same accuracy as those obtained from metallography.

A second exemplary application of the proposed method and system is in the area of composite material testing. A test sample of carbon fiber reinforced plastic (CFRP) was prepared having a planar, rectangular surface with dimensions of 100 mm×120 mm, and a thickness of 6.3 mm. A thin layer of paint was applied to the surface of the composite to obtain good ultrasonic generation in the thermoelastic regime.

The generation and detection set up used to verify the application included a multimode $CO_2$ laser to generate bulk ultrasonic waves. A Neodymium:Yttrium Aluminum Garnet (Nd:YAG) laser coupled to a Fabry-Perot interferometer for phase demodulation was used for ultrasonic detection. The laser spot size for generation was about 6.5 mm and that for detection was about 5 mm. The generation and detection spots were nearly superimposed, in accordance with the pulse-echo configuration. The frequency sensitivity range of the system was 1-10 MHz. Laser-ultrasonic measurements were performed to locate porosity areas inside the test object. A two-dimensional scan was performed on the surface by sweeping across the surface in parallel lines. Each measurement location was separated from that of neighbouring measurement locations by 1.47 mm.

Figure 8A:
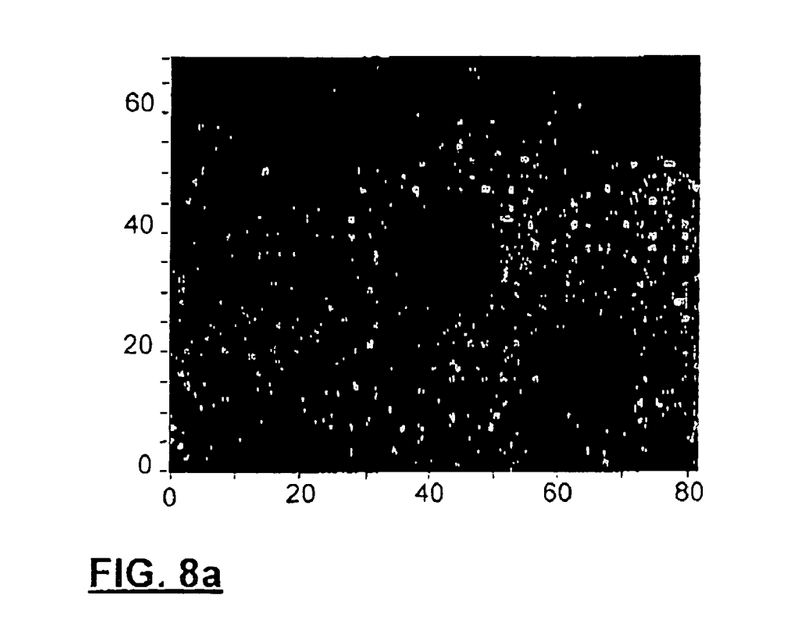
FIG. 8a is a C-scan image representing locations of porosity in a composite sample.

FIG. 8a is a greyscale C-scan image of the amplitude of the backwall echo. Circular spots S1-S3 are clearly observed with sizes of about 18 mm, identified as the locations of the pores in the test sample.

Figure 8B:
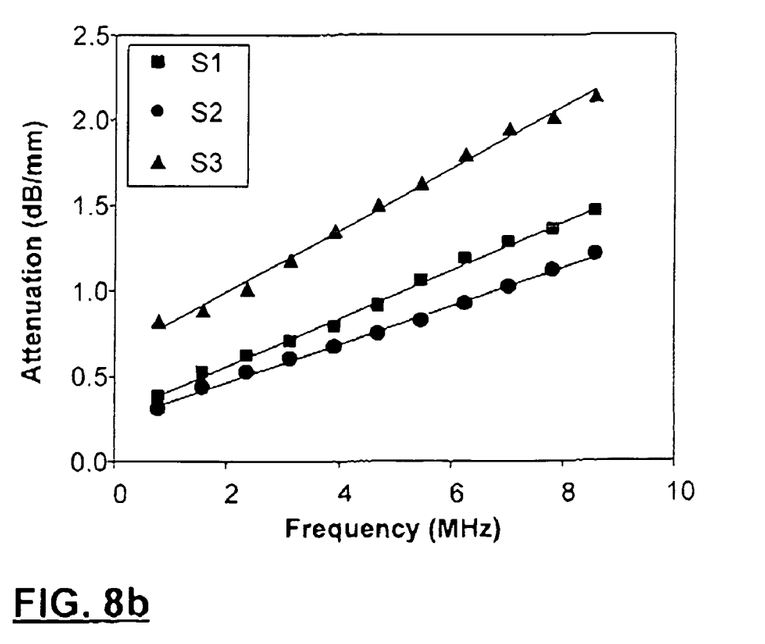
FIG. 8b is an attenuation spectra in the porosity areas of the composite sample.

FIG. 8b illustrates the attenuation spectra within the porosity areas S1, S2, and S3 identified in FIG. 8a. The reference spectrum used to obtain these attenuation spectra is taken from a backwall echo at a location where the material is known to be sound. It will be appreciated by those of skill in the art that ultrasonic attenuation is negligible in CFRP material at locations where no porosity or other defect is evident. In a composite material, the attenuation spectrum is expected to show a nearly linear behavior for a certain frequency range, in this case from 1 to 8 MHz. As is well known in the material sciences, the pore/volume fraction $P_v$ varies directly with the first derivative (i.e. the slope) of the attenuation spectrum within its linear region, where the attenuation is principally caused by a scattering effect. Accordingly:

$$P_v = c \frac{d\alpha(f)}{df} \qquad (4)$$

where c is a proportionality constant specific to the material and the pore geometry.

It will be noted that the use of this model to determine porosity content obviates correction for variation in signal strength, as a constant factor independent of frequency is eliminated by taking the derivative. Assuming that the value of c for this sample is 7.5 vol % mm MHz/dB, the estimated porosity contents in the areas S1, S2 and S3 are found to be 1.0, 0.8 and 1.5% respectively. These estimates are consistent with the nominal values associated with the preparation of the test sample.

Of course, numerous other applications of the method above can be considered without departing from the spirit and scope of the invention. In addition to the above embodiment with laser-ultrasonics, the proposed method can be applied using a different ultrasonic technique, such as with piezoelectric transducers or EMATs, for any type of waves (longitudinal, shear, surface, etc.) and any configuration (pulse echo, through-transmission, pitch-catch, etc.). For a given technique, wave mode and configuration, the test should be applied to the test material and to a reference material to produce a low attenuation reference spectrum.

The embodiments of the invention in which an exclusive property or privilege is claimed are defined as follows:

1. A method for using a measurement of ultrasonic attenuation to determine a material property of an object, the method comprising:
   (a) receiving an interaction signal from an ultrasound detector, at a detection location on the object in response to a broadband ultrasonic pulse impinging on the detection location, the ultrasonic pulse having been attenuated in travel through the object;
   (b) transforming a portion of the interaction signal corresponding to the attenuated pulse from the time domain to the frequency domain, to obtain an amplitude spectrum;
   (c) comparing the amplitude spectrum with a reference amplitude spectrum to obtain an attenuation spectrum, the reference amplitude spectrum produced using a reference piece having equivalent diffraction properties as the object with respect to the propagating broadband ultrasonic pulse, the reference amplitude spectrum being substantially free of attenuation;
   (d) determining a best fit of the attenuation spectrum to a model of frequency dependent attenuation that accounts for frequency independent variations of signal strength between the object and the reference piece, to obtain an attenuation parameter; and
   (e) using the attenuation parameter to compute a material property of the object that depends on the attenuation.

2. A method as claimed in claim 1 wherein (c) comprises selecting the reference piece having known attenuation parameters, and using the known attenuation parameters to correct for attenuation in the amplitude spectrum of the reference piece.

3. A method as claimed in claim 2 wherein selecting the reference piece comprises selecting a reference piece having a shape that matches the test object, and being made of a material having an ultrasonic velocity matching that of the test object.

4. A method as claimed in claim 1 wherein (c) comprises selecting the reference piece having substantially no attenuation.

5. A method as claimed in claim 1 further comprising determining the portion of the interaction signal by identifying a part of the interaction signal that corresponds to a single manifestation of the broadband ultrasonic pulse impinging on the detection location.

6. A method as claimed in claim 5 wherein determining the portion further comprises applying a window selection function for selecting part of the interaction signal that corresponds to a single manifestation of the broadband ultrasonic pulse impinging on the detection location.

7. A method as claimed in claim 6 wherein applying the window selection function further comprises using the cross-correlation of a standard profile of an ultrasonic pulse with the interaction signal to center the manifestation within the window.

8. A method as claimed in claim 5 wherein determining the portion comprises using prior knowledge of the test object to determine a coarse time window of the interaction signal including a single echo of the pulse to narrow a search of the portion within the interaction signal.

9. A method as claimed in claim 1 wherein receiving and transforming are repeatedly applied to a plurality of interaction signals from the object, and the method further comprises computing a mean of the plurality of signals.

10. A method according to claim 9 further comprising validating each of the echoes arid amplitude spectra using rejection criteria in both time and frequency domains.

11. A method according to claim 1 wherein identifying the best fit comprises comparing measures of fit of the attenuation spectrum to curves of the form:

$$\alpha(f) = \alpha_0 + af^m + bf^n$$

where $\alpha_0$ is an arbitrary amplitude offset that accounts for variations in signal strength, m and n are frequency powers associated with respective underlying mechanisms of the attenuation, and the parameters a and b are representative of contributions by the mechanisms involved relating to material properties.

12. A method according to claim 11 wherein the parameter a is zero.

13. A method according to claim 11 wherein fitting the attenuation spectrum comprises varying the attenuation parameters while keeping m and n fixed.

14. A method according to claim 1 wherein determining a best fit of the attenuation spectrum to a model uses the derivative of the attenuation spectrum to obtain an attenuation parameter.

15. A method according to claim 1 further comprising using a calibration curve to relate the attenuation parameter to a property of the object.

16. A method according to claim 1 wherein the material property is grain size in a polycrystalline solid.

17. A method according to claim 1 wherein the material property is porosity of a composite material.

18. A method according to claim 1 wherein the reference amplitude spectrum is produced from exactly the same generation and detection procedure as applied to the object.

19. A system for measuring ultrasonic attenuation to determine material properties of an object, comprising:
   (a) an ultrasonic pulse generation and detection set up for launching a broadband ultrasonic pulse into the object, and detecting the pulse after propagation through the object;
   (b) a receiver for digitizing an interaction signal of the detected ultrasonic pulse; and
   (c) a signal processor for:
   i transforming a part of the interaction signal corresponding to a single manifestation of the detected pulse from the time domain into the frequency domain to obtain an amplitude spectrum;
   ii computing an attenuation spectrum by comparing the amplitude spectrum with a reference amplitude spectrum, the reference amplitude spectrum being derived from a reference piece having equivalent diffraction properties as that of the object, the reference amplitude spectrum having known attenuation; and
   iii fitting the attenuation spectrum to a model of frequency dependent attenuation that accounts for frequency independent variations of signal strength between the object and the reference piece, to determine an attenuation parameter used for determining a property of the object.

20. A system according to claim 19 wherein the signal processor is further adapted to compute a mean of a plurality of interaction signals from the object at one or various locations to produce the amplitude spectrum.

21. A system according to claim 19 wherein the signal processor is further adapted to perform a time or frequency domain averaging process of the plurality of interaction signals to produce the amplitude spectrum.

22. A system according to claim 19 wherein the ultrasonic pulse generation and detection set up comprises a generation laser for generating the broadband ultrasonic pulse, and a detection laser coupled to an optical detection system for detecting the manifestation of the broadband ultrasonic pulse.

23. A system according to claim 22, wherein the generation laser and detection laser are directed onto a same side of the test object.

24. A system according to claim 19 further comprising a controlled motion system for scanning over a surface of the object to obtain attenuation spectra corresponding to attenuation along different paths through the object.

25. A system according to claim 24 wherein the attenuation spectra are used to create an image of the material property of the object.

* * * * *